(12) United States Patent
Nishiyama

(10) Patent No.: US 11,203,775 B2
(45) Date of Patent: Dec. 21, 2021

(54) METHOD FOR PREDICTING EFFECT OF DAIKENCHUTO AND METHOD FOR DETERMINING DOSAGE OF DAIKENCHUTO

(71) Applicant: TSUMURA & Co., Minato-ku (JP)

(72) Inventor: Mitsue Nishiyama, Ibaraki (JP)

(73) Assignee: TSUMURA & Co., Minato-ku (JP)

( * ) Notice: Subject to any disclaimer, the term of this patent is extended or adjusted under 35 U.S.C. 154(b) by 368 days.

(21) Appl. No.: 16/089,213

(22) PCT Filed: Mar. 15, 2017

(86) PCT No.: PCT/JP2017/010403
§ 371 (c)(1),
(2) Date: Sep. 27, 2018

(87) PCT Pub. No.: WO2017/169783
PCT Pub. Date: Oct. 5, 2017

(65) Prior Publication Data
US 2019/0119718 A1    Apr. 25, 2019

(30) Foreign Application Priority Data
Mar. 29, 2016  (JP) .............................. JP2016-066329

(51) Int. Cl.
*C12Q 1/06*     (2006.01)
*C12Q 1/689*    (2018.01)
(Continued)

(52) U.S. Cl.
CPC ................. *C12Q 1/06* (2013.01); *C12Q 1/02* (2013.01); *C12Q 1/025* (2013.01); *C12Q 1/24* (2013.01);
(Continued)

(58) Field of Classification Search
None
See application file for complete search history.

(56) References Cited

U.S. PATENT DOCUMENTS

2013/0260401 A1   10/2013   Kaneko et al.
2015/0126463 A1   5/2015    Hsiao et al.

FOREIGN PATENT DOCUMENTS

WO    WO 2012/073881 A1    6/2012
WO    WO 2015/062556 A1    5/2015

OTHER PUBLICATIONS

Peter J. Turnbaugh et al., "An Obesity-Associated Gut Microbiome with Increased Capacity for Energy Harvest", Nature, vol. 444, Dec. 28, 2006, pp. 1027-1031.
(Continued)

*Primary Examiner* — Diana B Johannsen
(74) *Attorney, Agent, or Firm* — Oblon, McClelland, Maier & Neustadt, L.L.P.

(57) ABSTRACT

Provided are a method for predicting the effect of Daikenchuto, a method for determining the dosage of Daikenchuto, etc. using an objective index by a method for predicting the effectiveness of Daikenchuto in a patient characterized by including the following steps (a) and (b): (a) a step of determining the ratio of the phylum Bacteroidetes to the phylum Firmicutes ($B_m/F_m$ ratio) in the intestine of the patient by analyzing the intestinal flora of the patient; and (b) a step of determining the effectiveness of Daikenchuto in the patient by comparison with criteria such that when the $B_m/F_m$ ratio is lower than a reference value, Daikenchuto is more effective, and when the $B_m/F_m$ ratio is higher than a reference value, Daikenchuto is less effective, and a method for determining the dosage of Daikenchuto for a patient characterized by including the following steps (a) and (e): (a) a step of determining the ratio of the phylum Bacteroidetes to the phylum Firmicutes ($B_m/F_m$ ratio) in the intestine
(Continued)

of the patient by analyzing the intestinal flora of the patient, and (e) a step of determining the dosage of Daikenchuto for the patient by decreasing the dosage of Daikenchuto for the patient when the $B_m/F_m$ ratio determined in the step (a) is a lower value than a reference value, and increasing the dosage of Daikenchuto for the patient when the $B_m/F_m$ ratio is a higher value than a reference value.

8 Claims, 1 Drawing Sheet

(51) Int. Cl.
| | | |
|---|---|---|
| *G01N 33/48* | (2006.01) | |
| *C12Q 1/02* | (2006.01) | |
| *C12Q 1/68* | (2018.01) | |
| *C12Q 1/24* | (2006.01) | |
| *C12N 1/20* | (2006.01) | |

(52) U.S. Cl.
CPC ............... *C12Q 1/68* (2013.01); *C12Q 1/689* (2013.01); *G01N 33/48* (2013.01); *C12N 1/20* (2013.01); *C12Q 2545/101* (2013.01)

(56) References Cited

OTHER PUBLICATIONS

Haiyin Jiang et al., "Altered Fecal Microbiota Composition in Patients With Major Depressive Disorder", Brain, Behavior, and Immunity, 2015, pp. 186-194.

Antonella Napolitano et al., "Novel Gut-Based Pharmacology of Metformin in Patients with Type 2 Diabetes Mellitus", Plos One, vol. 9, Issue 7, e100778, Jul. 2014, pp. 1-14.

Heetae Lee et al., "Effect of Metformin on Metabolic Improvement and Gut Microbiota", Applied and Environmental Microbiology, vol. 80, No. 19, Oct. 2014, pp. 5935-5943.

Meng Yu et al., "Variations in Gut Microbiota and Fecal Metabolic Phenotype Associated with Depression by 16S rRNA gene Sequencing and LC/MS-based Metabolomics", Journal of Pharmaceutical and Biomedical Analysis 138 (2017), pp. 231-239.

Nuria Farré et al., "Sleep Apnea Morbidity, A Consequence of Microbial-Immune Cross-Talk?", Commentary, 1 5 4 # 4 CHEST, Oct. 2018, pp. 754-759.

Extended European Search Report dated Nov. 18, 2019 in corresponding European Patent Application No. 17774327.5, 8 pages.

Falk Hildebrand et al., "A Comparative Analysis of the Intestinal Metagenomes Present in Guinea Pigs (*Cavia porcellus*) and Humans (*Homo sapiens*)", BMC Genomics, Biomed Central, vol. 13, No. 1, XP021106752, Sep. 28, 2012, pp. 1-11.

International Search Report dated Jun. 13, 2017, in PCT/JP2017/010403, filed Mar. 15, 2017.

Kim, K-A. et al., "Comparative Analysis of the Gut Microbiota in People with Different Levels of Ginsenoside Rb1 Degradation to Compound K", PLOS One, vol. 8, Issue 4, Apr. 2013, pp. 1-7.

Hasebe, T. et al., "Daikenchuto (TU-100) shapes gut microbiota architecture and increases the production of ginsenoside metabolite compound K", Pharmacology Research and Perspectives, vol. 4, Issue 1, e00215, 2016, pp. 1-10.

Haitori, M., "Intestinal Bacteria Play a Significant Role in the Medicinal Effects of Kampo Medicines", Journal of intestinal microbiology, vol. 26, 2012, pp. 159-169, with English abstract.

Otaguro, Y., "Sokkosei ga Kitai dekiru Kanpo Shoho", The Japanese Journal of Ryodoraku, Autonomic Nervous System, vol. 35, No. 6,7, 1990, p. 12 (168)-16(172).

Watanabe, J. et al., "Intestinal, portal, and peripheral profiles of daikenchuto (TU-100)'s active ingredients after oral administration", Pharmacology Research & Perspectives, vol. 3, Issue 5, e00165, 2015, pp. 1-12.

Kampo Igaku (Science of Kampo Medicine), vol. 38, No. 1, 2014, 2 pages.

Satoh,K. et al., "Mechanism of Atropine-Resistant Contraction Induced by *Dai-kenchu-to* in Guinea Pig Ileum", Japanese Journal of Pharmacology, vol. 86, 2001, pp. 32-37.

Qin, J. et al., "A human gut microbial gene catalogue established by metagenomic sequencing", Nature, vol. 464, Mar. 4, 2010, pp. 59-67.

Tokyo Japan Medical Association Academic Education Committee, "Nyumon Kampo Igaku (Introduction to KAMPO: Japanese Traditional Medicine)", 3 pages. (published Dec. 10, 2002).

METHOD FOR PREDICTING EFFECT OF DAIKENCHUTO AND METHOD FOR DETERMINING DOSAGE OF DAIKENCHUTO

TECHNICAL FIELD

The present invention relates to a method for predicting the effect of Daikenchuto and a method for determining the dosage of Daikenchuto by analyzing the intestinal flora of a patient.

BACKGROUND ART

In Western medical care (a treatment of a disease with a synthetic drug), in general, a disease is identified by a biochemical test or the like, and basically, the same drug is selected for patients with the same disease regardless of the physical conditions, body constitution, or the like of the patients. On the other hand, in Kampo medical care (a treatment with a Kampo preparation), different Kampo preparations are prescribed even for patients with the same disease of hypertension between a patient who is well built and has a relatively high physical strength and a patient who is elderly and has poor circulation. For example, for the former patient, Daisaikoto is used, and for the latter patient, Hachimijiogan is used. As the Kampo preparation, not only one component like a synthetic drug, but an extract extracted with an aqueous solvent from several crude drugs in combination is used, and therefore, a drug suitable for a patient even with the same disease can be selected according to the physical conditions or body constitution of the patient, the degree of progress of a disease, etc. For example, there are 9 types of Kampo preparations having an indication for common cold (Kakkonto, Shosaikoto, Saikokeishito, Maoto, Hochuekkito, Goshakusan, Jinsoin, Shomakakkonto, and Maobushisaishinto), and a medical doctor selects a Kampo preparation considered to be suitable for the patient by observing the conditions (a complexion, skin conditions, tongue conditions, whether the patient has a cold body part, how a physical strength is, whether the patient has vigor, etc.) of the patient in detail. These are the way of thinking not in the Western medical care which is a uniform therapeutic method. As described in NPL 1 which is a guide book for Kampo medical care, this diagnostic method is called "Shou" and is used as the basis of the treatment in the Kampo medical care.

However, unlike the Western medical science, which attaches great importance to objective biochemical test values, the diagnostic method based on Shou depends on the consultation technique of a medical doctor and therefore requires a skill based on many experiences. For example, according to NPL 2, Daikenchuto was not always effective in all patients. Due to this, also in Kampo medical care, not only the consultation technique of a medical doctor, but also an objective index capable of predicting effectiveness has been awaited.

CITATION LIST

Non Patent Literature

NPL 1: Nyumon Kampo Igaku (Introduction to KAMPO: Japanese Traditional Medicine), Tokyo Japan Medical Association Academic Education Committee, pp. 30-33

NPL 2: Kampo Igaku (Science of Kampo Medicine), vol. 38, No. 1, pp. 30-31, 2014

SUMMARY OF INVENTION

Technical Problem

An object of the present invention is to realize a tailor-made treatment in which the effectiveness of Kampo medical care is enhanced by using an objective index as well as the consultation technique of a medical doctor and a useless treatment is avoided so as to reduce the burden on a patient, and also an appropriate dosage for an individual patient can be estimated in advance.

Solution to Problem

As a result of intensive studies for achieving the above object, the present inventors found that the effectiveness of Daikenchuto has a relationship with the existence ratio of specific enteric bacteria, and thus completed the present invention.

That is, the present invention is directed to the following (1) to (9).

(1) A method for predicting the effectiveness of Daikenchuto in a patient, characterized by including the following steps (a) and (b):

(a) a step of determining the ratio of the phylum Bacteroidetes to the phylum Firmicutes ($B_m/F_m$ ratio) in the intestine of the patient by analyzing the intestinal flora of the patient; and (b) a step of determining the effectiveness of Daikenchuto in the patient by comparison with criteria such that when the $B_m/F_m$ ratio is lower than a reference value, Daikenchuto is more effective, and when the $B_m/F_m$ ratio is higher than a reference value, Daikenchuto is less effective.

(2) A method for predicting the effectiveness of Daikenchuto in a patient, characterized by including the following steps (c) and (d):

(c) a step of determining the ratio of the class Bacteroidetes to the class Clostridium ($B_k/C_k$ ratio) in the intestine of the patient by analyzing the intestinal flora of the patient; and (d) a step of determining the effectiveness of Daikenchuto in the patient by comparison with criteria such that when the $B_k/C_k$ ratio is lower than a reference value, Daikenchuto is more effective, and when the $B_k/C_k$ ratio is higher than a reference value, Daikenchuto is less effective.

(3) A method for selecting a Kampo preparation other than Daikenchuto for a patient in whom Daikenchuto is determined to be less effective by predicting the effectiveness of Daikenchuto by the above-mentioned method.

(4) A method for determining the dosage of Daikenchuto for a patient, characterized by including the following steps (a) and (e):

(a) a step of determining the ratio of the phylum Bacteroidetes to the phylum Firmicutes ($B_m/F_m$ ratio) in the intestine of the patient by analyzing the intestinal flora of the patient; and (e) a step of determining the dosage of Daikenchuto for the patient by decreasing the dosage of Daikenchuto for the patient when the $B_m/F_m$ ratio determined in the step (a) is a lower value than a reference value, and increasing the dosage of Daikenchuto for the patient when the $B_m/F_m$ ratio is a higher value than a reference value.

(5) A method for determining the dosage of Daikenchuto for a patient, characterized by including the following steps (c) and (f):

(c) a step of determining the ratio of the class Bacteroidetes to the class Clostridium ($B_k/C_k$ ratio) in the intestine of the patient by analyzing the intestinal flora of the patient; and (f) a step of determining the dosage of Daikenchuto for the patient by decreasing the dosage of Daikenchuto for the patient when the $B_k/C_k$ ratio determined in the step (c) is a lower value than a reference value, and increasing the dosage of Daikenchuto for the patient when the $B_k/C_k$ ratio is a higher value than a reference value.

(6) A kit for predicting the effectiveness of Daikenchuto in a patient, characterized by including:
a kit for analyzing the intestinal flora of the patient; and
a reference material describing a relationship between the ratio of the phylum Bacteroidetes to the phylum Firmicutes and whether Daikenchuto is more effective or less effective in the patient.

(7) A kit for predicting the effectiveness of Daikenchuto in a patient, characterized by including:
a kit for analyzing the intestinal flora of the patient; and
a reference material describing a relationship between the ratio of the class Bacteroidetes to the class Clostridium and whether Daikenchuto is more effective or less effective in the patient.

(8) A kit for determining the dosage of Daikenchuto for a patient, characterized by including:
a kit for analyzing the intestinal flora of the patient; and
a reference material describing a relationship between the ratio of the phylum Bacteroidetes to the phylum Firmicutes and the dosage and less effectiveness of Daikenchuto for the patient.

(9) A kit for determining the dosage of Daikenchuto for a patient, characterized by including:
a kit for analyzing the intestinal flora of the patient; and
a reference material describing a relationship between the ratio of the class Bacteroidetes to the class Clostridium and the dosage of Daikenchuto for the patient.

Advantageous Effects of Invention

According to the method of the present invention, the effectiveness or the dosage of Daikenchuto can be determined based on objective data, and therefore, more accurate Kampo medical treatment can be performed so as to avoid a useless treatment, and thus, the burden on a patient can be reduced.

Further, the kit of the present invention can be utilized for predicting the effectiveness of Daikenchuto in a patient or determining the dosage of Daikenchuto, and therefore is very useful for assisting a treatment or a diagnosis using Daikenchuto.

DESCRIPTION OF EMBODIMENTS

Figure 1:
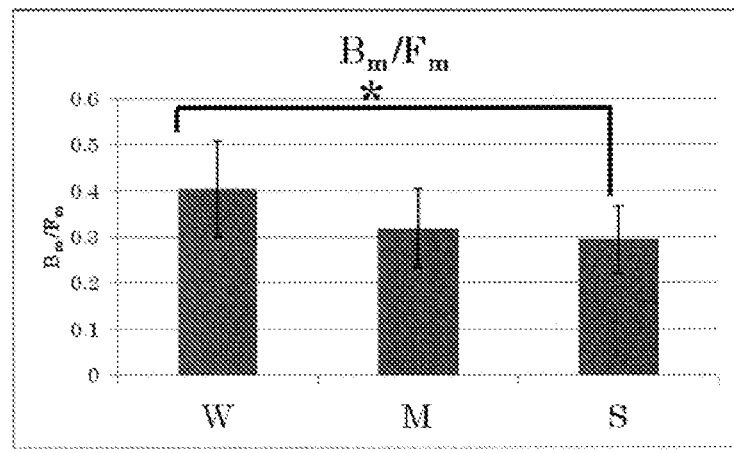
FIG. 1 is a graph showing a relationship between the ratio of the phylum Bacteroidetes to the phylum Firmicutes ($B_m/F_m$, ratio) in the intestine of guinea pigs and the effectiveness of Daikenchuto.

Daikenchuto related to the present invention is generally prepared from a powdered extract extracted from a mixed crude drug having a composition shown in Table 1 (sometimes referred to as "Koi-free Daikenchuto") and a powder sugar (Koi, English name: maltose) which was blended in the extract in an amount about 8 times the amount of the extract.

TABLE 1

| Japanese name (English name) | Blending amount (g) |
| --- | --- |
| Nikkyoku Kankyo (JP Processed Ginger) | 3 to 5 |
| Nikkyoku Ninjin (JP Ginseng) | 2 to 3 |
| Nikkyoku Sanshou (JP Zanthoxylum Fruit) | 1 to 2 |

As the Daikenchuto, a Daikenchuto preparation formulated into granules or the like by further adding a component permitted to be added as a pharmaceutical additive to the above-mentioned composition is also included. As such a formulated Daikenchuto preparation, commercially available products as pharmaceutical products for medical use such as Tsumura Daikenchuto extract granules (TJ-100: granules obtained by mixing a powdered liquid extract extracted from a mixed crude drug containing 5 g of JP Processed Ginger, 3 g of JP Ginseng, and 2 g of JP Zanthoxylum Fruit with a powder of the powder sugar in an amount 8 times the amount of this extract) from Tsumura & Co. can be exemplified.

Examples of the component permitted to be added as a pharmaceutical additive described above include excipients such as starch, lactose, white soft sugar, mannitol, carboxymethyl cellulose, cornstarch, and an inorganic salt, a disintegrating agent, a surfactant, a lubricant, a fluidity promoting agent, a corrigent, a coloring agent, and a flavor.

It is said that this Daikenchuto can be expected to have an effect on a patient who complains of abdominal pain due to cold abdomen and abdominal bloating, has a lowered physical strength and a thin abdominal wall, and shows weak intestinal peristalsis, so-called reduced gastrointestinal motility. Specific examples of diseases include constipation, intestinal motility paralysis, Crohn's disease, inflammatory bowel diseases, ulcerative colitis, and postoperative ileus.

The method for predicting the effect of Daikenchuto on a patient of the present invention includes the following steps (a) and (b) (hereinafter this is referred to as "the effect prediction method of the present invention").

(a) a step of determining the ratio of the phylum Bacteroidetes to the phylum Firmicutes ($B_m/F_m$ ratio) in the intestine of the patient by analyzing the intestinal flora of the patient (b) a step of determining the effectiveness of Daikenchuto in the patient by comparison with criteria such that when the $B_m/F_m$ ratio is lower than a reference value, Daikenchuto is more effective, and when the $B_m/F_m$ ratio is higher than a reference value, Daikenchuto is less effective In the above step (a), the analysis of the intestinal flora of the patient may be performed by a conventionally known analytical method. Examples of such a conventionally known analytical method include a culture method, a PCR method, and a comprehensive analytical method using a next-generation sequencer.

Specifically, in the analysis of the intestinal flora, the feces of a patient are collected and analyzed by a culture method, a molecular biological technique, or the like. In the analysis, it is required to detect at least microorganisms of the phylum Bacteroidetes and the phylum Firmicutes and analyze the appearance frequency or the like, and, for example, it is preferred to detect microorganisms shown in the following Table 2 and analyze the appearance frequency of these microorganisms. More specifically, Bacteroidetes Bacteroidia is selected as a microorganism of the phylum Bacteroidetes, and Firmicutes Bacilli, Firmicutes Clostridia, Firmicutes Erysipelotrichi are selected as microorganisms of the phylum Firmicutes, and the ratio of the phylum Bacteroidetes to the phylum Firmicutes may be determined based on the appearance frequency of these microorganisms. Incidentally, the microorganisms shown in Table 2 and the genetic information thereof can be obtained from a depositary institution such as ATCC or various databases. Further, primers and the like for the analysis can be easily prepared based on these microorganisms or the genetic information by those skilled in the art.

TABLE 2

| Phylum | Class |
| --- | --- |
| Euryarchaeota | Methanobacteria |
|  | Methanomicrobia |
|  | Thermoplasmata |
| Actinobacteria | Actinobacteria |
|  | Coriobacteriia |
| Bacteroidetes | Bacteroidia |
| Cyanobacteria | 4C0d-2 |
| Deferribacteres | Deferribacteres |
| Elusimicrobia | Elusimicrobia |
| Firmicutes | Bacilli |
|  | Clostridia |
|  | Erysipelotrichi |
| Lentisphaerae | [Lentisphaeria] |
| Proteobacteria | Alphaproteobacteria |
|  | Betaproteobacteria |
|  | Deltaproteobacteria |
|  | Epsilonproteobacteria |
|  | Gammaproteobacteria |
| Spirochaetes | Spirochaetes |
| Synergistetes | Synergistia |
| TM7 | TM7-3 |
| Tenericutes | Mollicutes |
|  | RF3 |
| Verrucomicrobia | Opitutae |
|  | Verrucomicrobiae |

In the above step (b), the ratio of the phylum Bacteroidetes to the phylum Firmicutes ($B_m/F_m$ ratio) determined in the above step (a) is compared with a reference value, and the effectiveness of Daikenchuto in the patient is determined by comparison with criteria such that when the $B_m/F_m$ ratio is lower than a reference value, Daikenchuto is more effective, and when the $B_m/F_m$ ratio is higher than a reference value, Daikenchuto is less effective.

Specifically, the reference value for which Daikenchuto is more effective is set to 0.29, and when the $B_m/F_m$ ratio is lower than the reference value, it is determined that Daikenchuto is more effective. Further, the reference value for which Daikenchuto is less effective is set to 0.4, and when the $B_m/F_m$ ratio is higher than the reference value, it is determined that Daikenchuto is less effective.

Incidentally, in the case where it is determined that Daikenchuto is less effective in the above, a Kampo preparation suitable for the patient other than Daikenchuto is selected. For example, in the case where the patient shows reduced gastrointestinal motility, a Kampo preparation is selected from the group consisting of Daiobotampito, Junchoto, Tokakujokito, Bofutsushosan, Choijokito, Daiokanzoto, Tsudosan, San'oshashinto, and Mashiningan.

The effect prediction method of the present invention described above can utilize a kit for predicting the effect of Daikenchuto on a patient including components as described below.

a kit for analyzing the intestinal flora of the patient a reference material describing a relationship between the ratio of the phylum Bacteroidetes to the phylum Firmicutes and whether Daikenchuto is more effective or less effective in the patient.

In the above-mentioned kit, as the kit for analyzing the intestinal flora of the patient, a commercially available kit such as an intestinal flora test kit (manufactured by Molecular Physiological Chemistry Laboratory, Inc.) or Mykinso (manufactured by Cykinso, Inc.), a kit including a sample collection container, various primers, various reagents, etc. to be used for the analysis of the intestinal flora described above, and the like are exemplified.

Further, in the above-mentioned kit, as the reference material describing a relationship between the ratio of the phylum Bacteroidetes to the phylum Firmicutes and whether Daikenchuto is more effective or less effective in the patient, a sheet of paper or the like on which the $B_m/F_m$ ratio capable of determining whether Daikenchuto is more effective or less effective or a graph or the like based on the ratio has been printed, an electronic medium such as a CD, a DVD, a USB memory, a memory card, or a hard disk in which such data have been stored, and the like are exemplified.

In addition, the dosage of Daikenchuto for the patient can be determined in the following step (e) from the ratio of the phylum Bacteroidetes to the phylum Firmicutes ($B_m/F_m$ ratio) determined in the above-mentioned step (a) (hereinafter this is referred to as "the dosage determination method of the present invention").

(e) a step of determining the dosage of Daikenchuto for the patient by decreasing the dosage of Daikenchuto for the patient when the $B_m/F_m$ ratio determined in the step (a) is a lower value than a reference value, and increasing the dosage of Daikenchuto for the patient when the $B_m/F_m$ ratio is a higher value than a reference value.

Specifically, the reference value for which the dosage of Daikenchuto is decreased is set to 0.29, and when the $B_m/F_m$ ratio is lower than the reference value, the dosage of Daikenchuto is decreased. Further, the reference value for which the dosage of Daikenchuto is increased is set to 0.4, and when the $B_m/F_m$ ratio is higher than the reference value, the dosage of Daikenchuto is increased.

Incidentally, a general dosage of Daikenchuto to serve as the basis is not particularly limited and may be appropriately set according to the compositional ratio of Daikenchuto to be used, or the body weight or the like of a patient as a target of administration. For example, when TSUMURA Daikenchuto extract granules (TJ-100, manufactured by Tsumura & Co.) is used, the dosage of Daikenchuto is 15 g per day for a Japanese male adult (average body weight: 60 kg), and 22 g per day for an American male adult (average body weight: 87 kg).

As for a specific dosage of Daikenchuto for a patient, for example, when the daily dosage determined based on the body weight of a patient is 15 g, the dosage for a patient who has a $B_m/F_m$ ratio lower than 0.29 is 7.5 g which is half the daily dosage, and for a patient who has a $B_m/F_m$ ratio higher than 0.4 is 30 g which is twice the daily dosage. Incidentally, for a patient who has a $B_m/F_m$ ratio higher than 0.4, a Kampo preparation suitable for the patient other than Daikenchuto is selected instead of doubling the dosage.

The dosage determination method of the present invention described above can utilize a kit for determining the dosage of Daikenchuto for a patient including components as described below.

a kit for analyzing the intestinal flora of the patient a reference material describing a relationship between the ratio of the phylum Bacteroidetes to the phylum Firmicutes and the dosage of Daikenchuto for the patient.

In the above-mentioned kit, as the kit for analyzing the intestinal flora of the patient, the same kit as the foregoing can be used.

Further, in the above-mentioned kit, as the reference material describing a relationship between the ratio of the phylum Bacteroidetes to the phylum Firmicutes and the dosage of Daikenchuto for the patient, a sheet of paper or the like on which the $B_m/F_m$ ratio capable of determining the dosage of Daikenchuto or a graph or the like based on the ratio has been printed, an electronic medium such as a CD, a DVD, a USB memory, a memory card, or a hard disk in which such data have been stored, and the like are exemplified.

Incidentally, the ratio of the class Bacteroidetes to the class Clostridium ($B_k/C_k$ ratio) has a relationship with the effectiveness of Daikenchuto and the dosage of Daikenchuto in the same manner as the ratio of the phylum Bacteroidetes to the phylum Firmicutes ($B_m/F_m$ ratio).

Therefore, in the effect prediction method of the present invention and the dosage determination method of the present invention described above and the kit to be used for these methods, when the ratio of the class Bacteroidetes to the class Clostridium is determined by an analysis of the intestinal flora of a patient and the respective reference values are changed from the ratio of the phylum Bacteroidetes to the phylum Firmicutes ($B_m/F_m$ ratio) to the ratio of the class Bacteroidetes to the class Clostridium ($B_k/C_k$ ratio), the effectiveness of Daikenchuto can be predicted or the dosage of Daikenchuto can be determined based on the $B_k/C_k$ ratio.

In the analysis of the intestinal flora of a patient, it is required to detect at least microorganisms of the class Bacteroidetes and the class Clostridium and analyze the appearance frequency or the like, and, for example, it is preferred to detect microorganisms shown in Table 2 and analyze the appearance frequency of these microorganisms. More specifically, Bacteroidetes Bacteroidia is selected as a microorganism of the class Bacteroidetes, Firmicutes Clostridia is selected as a microorganism of the class Clostridium, and the ratio of the class Bacteroidetes to the class Clostridium may be determined based on the appearance frequency of these microorganisms.

In the case where the ratio of the phylum Bacteroidetes to the phylum Firmicutes ($B_m/F_m$ ratio) in the effect prediction method of the present invention is replaced with the ratio of the class Bacteroidetes to the class Clostridium ($B_k/C_k$ ratio), the reference value for which Daikenchuto is more effective becomes 0.329, and the reference value for which Daikenchuto is less effective becomes 0.454.

Further, in the case where the ratio of the phylum Bacteroidetes to the phylum Firmicutes ($B_m/F_m$ ratio) in the dosage determination method of the present invention is replaced with the ratio of the class Bacteroidetes to the class Clostridium ($B_k/C_k$ ratio), the reference value for which the dosage of Daikenchuto is decreased becomes 0.329, and the reference value for which the dosage of Daikenchuto is increased becomes 0.454.

EXAMPLES

Hereinafter, the present invention will be described in detail with reference to Examples, however, the present invention is by no means limited to these Examples.

Example 1

Relationship between Intestinal Flora and Effectiveness of Daikenchuto:
(1) Preparation of Sample 151 Hartley guinea pigs (male) of 5 to 8 weeks of age which were previously acclimated were used as samples. After these guinea pigs were euthanized by decapitation, the contents (feces) recovered from the cecum were used in an analysis of the intestinal flora. Further, the distal colon was excised and used in the following Magnus test.
(2) Analysis of Intestinal Flora DNA was extracted from the contents of the cecum recovered in the above (1) by a known method. 16S rDNA gene contained in this DNA was amplified using Advantage HF2 (manufactured by Takara Bio, Inc.). After amplification, the amplified product was purified using AMPure XP beads (manufactured by NIPPON Genetics Co., Ltd.).

A library was prepared from the thus obtained amplified product using Nextera XT Index Kit (manufactured by Illumina, Inc.), the base sequence was determined using MiSeq (manufactured by Illumina, Inc.), and an unnecessary sequence was trimmed off as needed.

Annotation was performed for the base sequence after trimming by 16S rRNA gene database (Greengenes the 16S rRNA Gene Database) search, classification was performed for each sample, and the frequency of appearance (appearance frequency) at each level of the phylum, class, or the like was counted.

The phylum Bacteroidetes and the phylum Firmicutes occupy the majority of the enteric bacteria of the guinea pig, and particularly, the class Bacteroidetes and the class Clostridium occupy 78.4% (n=151) of the entire flora. Incidentally, the appearance frequency of the enteric bacteria of the guinea pig is shown in Table 3.

TABLE 3

| Phylum | Class | Appearance frequency (%) |
| --- | --- | --- |
| Euryarchaeota | Methanobacteria | 0.152 ± 0.099 |
| | Methanomicrobia | 0.001 ± 0.004 |
| | Thermoplasmata | 0.001 ± 0.005 |
| Actinobacteria | Actinobacteria | 0.065 ± 0.181 |
| | Coriobacteriia | 0.52 ± 0.315 |
| Bacteroidetes | Bacteroidia | 20.938 ± 4.253 |
| Cyanobacteria | 4C0d-2 | 0.194 ± 0.217 |
| Deferribacteres | Deferribacteres | 0.04 ± 0.052 |
| Elusimicrobia | Elusimicrobia | 0.055 ± 0.067 |
| Firmicutes | Bacilli | 0.112 ± 0.222 |
| | Clostridia | 58.095 ± 7.097 |
| | Erysipelotrichi | 7.135 ± 6.359 |
| Lentisphaerae | [Lentisphaeria] | 0.007 ± 0.015 |
| Proteobacteria | Alphaproteobacteria | 1.074 ± 0.95 |
| | Betaproteobacteria | 0.086 ± 0.054 |
| | Deltaproteobacteria | 0.736 ± 0.244 |
| | Epsilonproteobacteria | 0.001 ± 0.006 |
| | Gammaproteobacteria | 0.049 ± 0.167 |
| Spirochaetes | Spirochaetes | 0.25 ± 0.171 |
| Synergistetes | Synergistia | 0.842 ± 0.719 |
| TM7 | TM7-3 | 0.942 ± 0.506 |
| Tenericutes | Mollicutes | 0.656 ± 0.332 |
| | RF3 | 0.054 ± 0.067 |
| Verrucomicrobia | Opitutae | 0.342 ± 0.628 |
| | Verrucomicrobiae | 2.673 ± 2.108 |

(3) Magnus Test

As described below, a Magnus test was performed using the distal colon excised in the above (1) based on the method described in the report (Jpn. J. Pharmacol. 86, 32-37 (2001)).

The distal colon excised in the above (1) was suspended in a Magnus tube of a Magnus apparatus by applying an addition of 3 g in the longitudinal muscle direction, and a mixed gas of 95% oxygen and 5% carbon dioxide and a Krebs-Henseleit solution at 37° C. were introduced into the tube. During the test, the Magnus tube was maintained at 32° C. in a thermostat bath.

The length of the distal colon was recorded 60 minutes after the Krebs-Henseleit solution was introduced (after equilibration). Subsequently, a $10^{-6}$ mol/L acetylcholine solution was added, and the contraction length of the distal colon at this time was recorded. Thereafter, the distal colon was washed with the Krebs-Henseleit solution, and then, a 0.004 to 1.628 mg/mL suspension of Koi-free Daikenchuto produced by the method described in The Japanese Pharmacopoeia was added thereto, and the contraction length of the distal colon at this time was recorded.

Further, the contraction length of the distal colon when the acetylcholine solution was introduced was assumed to be 100%, and the contraction ratio versus acetylcholine when Daikenchuto was introduced with respect to this was determined. Subsequently, a contraction ratio was estimated for each individual at the time of administration with a tentative $EC_{50}$. Incidentally, this $EC_{50}$ of Daikenchuto corresponds to a concentration when a person takes 5 g (corresponding to a dose when dividing the daily dosage 15 g by 3) of Daikenchuto (TJ-100, manufactured by Tsumura & Co.) before meal and Daikenchuto is assumed to reach the colon as it is.

(4) Results

Based on the results of the above (1) to (3), a relationship between the contraction ratio of the intestine by Daikenchuto and the ratio of enteric bacteria, the amount of enteric bacteria, or the like was examined.

FIG. 1 shows the $B_m/F_m$ ratio in each group when an individual in which the contraction ratio of the intestine by Daikenchuto was 37.024±5.093% was grouped in a W group (week: the effectiveness is low), an individual in which the contraction ratio was 52.142±5.065% was grouped in an M group (middle: the effectiveness is moderate), and an individual in which the contraction ratio was 68.556±5.359% was grouped in an S group (strong: the effectiveness is high). The $B_m/F_m$ ratio was 0.4±0.1 in the W group, 0.32±0.085 in the M group, and 0.29±0.07 in the S group, and it was found that the $B_m/F_m$ ratio is smaller in the group with a stronger contraction. A statistically significant difference (p<0.000267) was confirmed between the W group and the S group in a Welch's t test.

Figure 2:
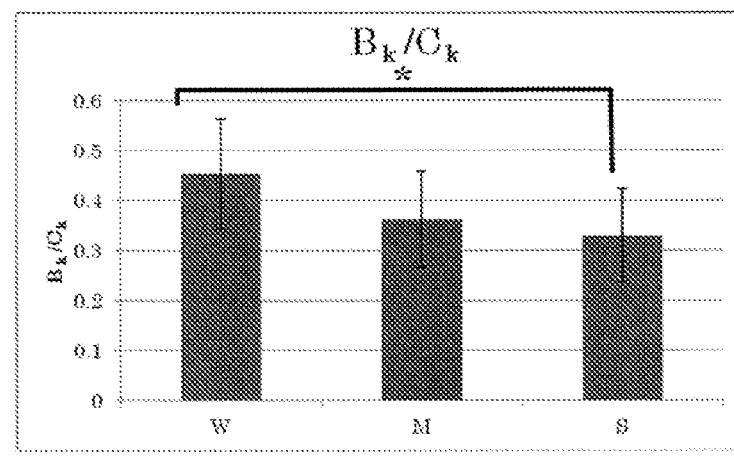
FIG. 2 is a graph showing a relationship between the ratio of the class Bacteroidetes to the class Clostridium ($B_k/C_k$ ratio) in the intestine of guinea pigs and the effectiveness of Daikenchuto.

FIG. 2 shows the $B_k/C_k$ ratio in each group when an individual in which the contraction ratio of the intestine by Daikenchuto was 37.024±5.093% was grouped in a W group (week: the effectiveness is low), an individual in which the contraction ratio was 52.142±5.065% was grouped in an M group (middle: the effectiveness is moderate), and an individual in which the contraction ratio was 68.556±5.359% was grouped in an S group (strong: the effectiveness is high). The $B_k/C_k$ ratio was 0.454±0.111 in the W group, 0.362±0.096 in the M group, and 0.329±0.094 in the S group, and it was found that the $B_k/C_k$ ratio is smaller in the group with a stronger contraction in the same manner as the $B_m/F_m$ ratio. A statistically significant difference (p<0.000262) was confirmed between the W group and the S group in a Welch's t test.

Figure 3:
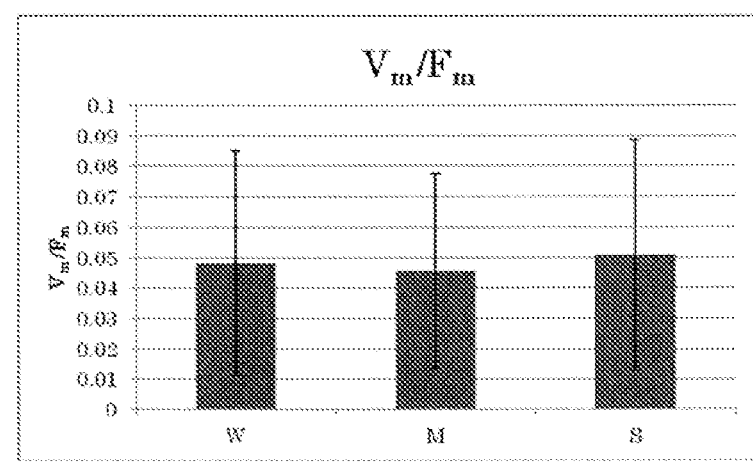
FIG. 3 is a graph showing a relationship between the ratio of the phylum Verrucomicrobia to the phylum Firmicutes ($V_m/F_m$, ratio) in the intestine of guinea pigs and the effectiveness of Daikenchuto.

It was found that the $B_k/C_k$ ratio is smaller in the group with a stronger intestinal contraction in the same manner as the $B_m/F_m$ ratio. Incidentally, a relationship was not observed between the contraction ratio of the intestine by Daikenchuto and the ratio of enteric bacteria, the amount of enteric bacteria, or the like other than the phylum Bacteroidetes and the phylum Firmicutes, and the class Bacteroidetes and the class Clostridium. One example of the enteric bacteria having no relationship (the ratio of the phylum Verrucomicrobia to the phylum Firmicutes ($V_m/F_m$ ratio)) is shown in FIG. 3.

Incidentally, it is known that also in the intestinal flora of humans, the amount of the phylum Bacteroidetes and the phylum Firmicutes is large (Nature, Vol. 464, 4 Mar. 2010, doi:10.1038/nature08821), and it is presumed that these results are applicable to humans.

From the above results, it was found that the effectiveness of Daikenchuto and the $B_m/F_m$ ratio or the $B_k/C_k$ ratio have a relationship with each other. It was also found that by determining the $B_m/F_m$ ratio or the $B_k/C_k$ ratio of a patient, the dosage of Daikenchuto for the patient can be determined. Then, the $B_m/F_m$ ratio at which Daikenchuto is more effective was determined to be lower than 0.29, and the $B_m/F_m$ ratio at which Daikenchuto is less effective was determined to be higher than 0.4. In addition, the $B_m/F_m$ ratio at which the dosage of Daikenchuto is decreased was determined to be lower than 0.29, and the $B_m/F_m$ ratio at which the dosage of Daikenchuto is increased was determined to be higher than 0.4. Further, the $B_k/C_k$ ratio at which Daikenchuto is more effective was determined to be lower than 0.329, and the $B_k/C_k$ ratio at which Daikenchuto is less effective was determined to be higher than 0.454. Still further, the $B_k/C_k$ ratio at which the dosage of Daikenchuto is decreased was determined to be lower than 0.329, and the $B_k/C_k$ ratio at which the dosage of Daikenchuto is increased was determined to be higher than 0.454.

Example 2

Kit for Predicting Effectiveness of Daikenchuto in Patient and Determining Dosage of Daikenchuto for Patient A kit for predicting the effectiveness of Daikenchuto in a patient and determining the dosage of Daikenchuto for a patient was prepared by placing a commercially available kit for analyzing intestinal flora and a sheet of paper on which a relationship between the ratio of the phylum Bacteroidetes to the phylum Firmicutes and whether Daikenchuto is more effective or less effective in a patient and a relationship between the ratio and the dosage for a patient are printed in one package.

By using this kit, it became possible to effectively perform a treatment of a patient with Daikenchuto.

Example 3

Kit for Predicting Effectiveness of Daikenchuto in Patient and Determining Dosage of Daikenchuto for Patient A kit for predicting the effectiveness of Daikenchuto in a patient and determining the dosage of Daikenchuto for a patient was prepared by placing a commercially available kit for analyzing intestinal flora and a sheet of paper on which a relationship between the ratio of the class Bacteroidetes to the class Clostridium and whether Daikenchuto is more effective or less effective in a patient and a relationship between the ratio and the dosage for a patient are printed in one package.

INDUSTRIAL APPLICABILITY

The present invention can be utilized in a treatment of a patient using Daikenchuto.

The invention claimed is:

1. A method for treating a patient undergoing Kampo medical care wherein said method comprises:
   obtaining an intestinal flora sample from the feces of the patient, wherein said Kampo medical care of said patient comprises administration of Daikenchuto;
   determining a ratio of the phylum Bacteroidetes to the phylum Firmicutes ($B_m/F_m$ ratio) in the intestine of the patient by analyzing the intestinal flora sample of the patient;
   determining the effectiveness of Daikenchuto in the patient by comparison with criteria such that when the $B_m/F_m$ ratio is lower than a reference value, Daikenchuto is more effective, and when the $B_m/F_m$ ratio is higher than a reference value, Daikenchuto is less effective, wherein the reference value for which Daikenchuto is more effective is 0.29, and the reference value for which Daikenchuto is less effective is 0.4; and
   continuing administration of Daikenchuto unless Daikenchuto is determined to be less effective in which case administration of Daikenchuto is discontinued and the patient is administered a Kampo preparation selected from the group consisting of Daiobotampito, Junchoto, Tokakujokito, Bofutsushosan, Choijokito, Daiokanzoto, Tsudosan, San'oshashinto, and Mashiningan.

2. A method for treating a patient undergoing Kampo medical care wherein said method comprises:
   obtaining an intestinal flora sample from the feces of the patient, wherein said Kampo medical care of said patient comprises administration of Daikenchuto;
   determining a ratio of the class Bacteroidetes to the class *Clostridium* ($B_k/C_k$ ratio) in the intestine of the patient by analyzing the intestinal flora sample of the patient;
   determining the effectiveness of Daikenchuto in the patient by comparison with criteria such that when the $B_k/C_k$ ratio is lower than a reference value, Daikenchuto is more effective, and when the $B_k/C_k$ ratio is higher than a reference value, Daikenchuto is less effective, wherein the reference value for which Daikenchuto is more effective is 0.329, and the reference value for which Daikenchuto is less effective is 0.454; and
   continuing administration of Daikenchuto unless Daikenchuto is determined to be less effective in which case administration of Daikenchuto is discontinued and the patient is administered a Kampo preparation selected from the group consisting of Daiobotampito, Junchoto, Tokakujokito, Bofutsushosan, Choijokito, Daiokanzoto, Tsudosan, San'oshashinto, and Mashiningan.

3. A method for treating a patient undergoing Kampo medical care comprising administering a dosage of Daikenchuto wherein said method comprises:
   obtaining an intestinal flora sample from the feces of the patient, wherein said Kampo medical care of said patient comprises administration of Daikenchuto;
   determining a ratio of the phylum Bacteroidetes to the phylum Firmicutes ($B_m/F_m$ ratio) in the intestine of the patient by analyzing the intestinal flora sample of the patient; and
   adjusting the dosage of Daikenchuto for the patient by decreasing the dosage of Daikenchuto for the patient when the $B_m/F_m$ ratio is a lower value than a reference value, and increasing the dosage of Daikenchuto for the patient when the $B_m/F_m$ ratio is a higher value than a reference value, wherein the reference value for which the dosage of Daikenchuto is decreased is 0.29, and the reference value for which the dosage of Daikenchuto is increased is 0.4.

4. A method for treating a patient undergoing Kampo medical care wherein said method comprises:
   obtaining an intestinal flora sample from the feces of the patient, wherein said Kampo medical care of said patient comprises administration of Daikenchuto;
   determining a ratio of the class Bacteroidetes to the class *Clostridium* ($B_k/C_k$ ratio) in the intestine of the patient by analyzing the intestinal flora sample of the patient; and
   adjusting the dosage of Daikenchuto for the patient by decreasing the dosage of Daikenchuto for the patient when the $B_k/C_k$ ratio is a lower value than a reference value, and increasing the dosage of Daikenchuto for the patient when the $B_k/C_k$ ratio is a higher value than a reference value, wherein the reference value for which the dosage of Daikenchuto is decreased is 0.329, and the reference value for which the dosage of Daikenchuto is increased is 0.454.

5. The method of claim 1, wherein the patient undergoing Kampo medical care has a disease selected from the group consisting of constipation, intestinal motility paralysis, Crohn's disease, inflammatory bowel diseases, ulcerative colitis, and postoperative ileus.

6. The method of claim 2, wherein the patient undergoing Kampo medical care has a disease selected from the group consisting of constipation, intestinal motility paralysis, Crohn's disease, inflammatory bowel diseases, ulcerative colitis, and postoperative ileus.

7. The method of claim 3, wherein the patient undergoing Kampo medical care has a disease selected from the group consisting of constipation, intestinal motility paralysis, Crohn's disease, inflammatory bowel diseases, ulcerative colitis, and postoperative ileus.

8. The method of claim 4, wherein the patient undergoing Kampo medical care has a disease selected from the group consisting of constipation, intestinal motility paralysis, Crohn's disease, inflammatory bowel diseases, ulcerative colitis, and postoperative ileus.

* * * * *

UNITED STATES PATENT AND TRADEMARK OFFICE
CERTIFICATE OF CORRECTION

PATENT NO. : 11,203,775 B2
APPLICATION NO. : 16/089213
DATED : December 21, 2021
INVENTOR(S) : Nishiyama It is certified that error appears in the above-identified patent and that said Letters Patent is hereby corrected as shown below:

In the Specification

Column 5, Line 9, delete "Erysipelotrichi" and insert -- Erysipelotrichia --;

Column 5, Line 33, delete "Erysipelotrichi" and insert -- Erysipelotrichia --.

Column 8, Line 54, delete "Erysipelotrichi" and insert -- Erysipelotrichia --.

In the Claims

Column 11, Claim 3, Lines 55-56, delete "comprising administering a dosage of Daikenchuto".

Signed and Sealed this
Seventh Day of June, 2022

Katherine Kelly Vidal
*Director of the United States Patent and Trademark Office*